US005697901A

United States Patent [19]
Eriksson

[11] Patent Number: 5,697,901
[45] Date of Patent: Dec. 16, 1997

[54] GENE DELIVERY BY MICRONEEDLE INJECTION

[75] Inventor: Elof Eriksson, 5 Lanark Rd., Welesley, Mass. 02181

[73] Assignee: Elof Eriksson, Wellesley Hills, Mass.

[21] Appl. No.: 445,265

[22] Filed: May 19, 1995

Related U.S. Application Data

[63] Continuation-in-part of Ser. No. 76,550, Jun. 11, 1993, abandoned, which is a continuation-in-part of Ser. No. 897,357, Jun. 11, 1992, Pat. No. 5,423,778, which is a continuation-in-part of Ser. No. 707,248, May 22, 1991, Pat. No. 5,152,757, which is a continuation of Ser. No. 451,957, Dec. 14, 1989, abandoned.

[51] Int. Cl.$^6$ ............................................. C12N 15/00
[52] U.S. Cl. ...................... 604/46; 435/172.1; 435/240.1
[58] Field of Search ............................. 604/46, 191, 890.1, 604/891.1, 51; 435/172.1, 172.2, 172.3, 240.1, 240.2, 240, 241

[56] References Cited

U.S. PATENT DOCUMENTS

| | | |
|---|---|---|
| 3,026,874 | 3/1962 | Stevens . |
| 3,288,140 | 11/1966 | McCarthy . |
| 3,580,254 | 5/1971 | Stuart . |
| 3,814,097 | 6/1974 | Ganderson et al. . |
| 4,304,866 | 12/1981 | Green et al. . |
| 4,767,746 | 8/1988 | Catsimpoolas et al. . |
| 4,784,737 | 11/1988 | Ray et al. .............................. 604/30 X |

(List continued on next page.)

FOREIGN PATENT DOCUMENTS

| | | |
|---|---|---|
| 641061 | 8/1950 | United Kingdom . |
| WO90/11092 | 10/1990 | WIPO . |
| WO92/15676 | 9/1992 | WIPO . |

OTHER PUBLICATIONS

Breuing, et al., "Healing of Partial Thickness Porcine Skin Wounds in a Liquid Environment," *Journal of Surgical Research* 52:50–58 (1992).

Davis, H.L., et al., "Direct Gene Transfer in Skeletal Muscle: Plasmid DNA–Based Immunization Against the Hepatitis B Virus Surface Antigen," *Vaccine*, 12:1503–1509 (1994).

(List continued on next page.)

*Primary Examiner*—Michael Powell Buiz
*Assistant Examiner*—A. T. Nguyen
*Attorney, Agent, or Firm*—Quarles & Brady

[57] ABSTRACT

Direct gene transfer of genetic material into an external or internal target cell site ("microseeding"), in optional combination with a wound treatment chamber, are particularly effective as a way of obtaining long term expression of native or non-native polypeptides in a host. A wide variety of proteins and materials can be expressed, either for secretion into the general blood and lymphatic system, or to alter the properties of the protein, for example, to not express proteins eliciting an immune response. The use of the optional wound chamber system for gene transfer to skin target sites also allows non-invasive assessment of the success of transfer by assaying for the presence of the expressed protein in wound fluid, in contrast to the prior art use of invasive techniques, such as biopsies, in order to achieve the same assessment of early expression.

21 Claims, 7 Drawing Sheets

U.S. PATENT DOCUMENTS

| | | | |
|---|---|---|---|
| 4,788,971 | 12/1988 | Quisno. | |
| 4,847,193 | 7/1989 | Richards et al.. | |
| 4,868,116 | 9/1989 | Morgan et al.. | |
| 4,980,286 | 12/1990 | Morgan et al. | 435/172.3 |
| 5,036,006 | 7/1991 | Sanford et al. | 435/172.1 |
| 5,152,757 | 10/1992 | Eriksson. | |
| 5,225,750 | 7/1993 | Higuchi et al. | 318/280 |
| 5,262,128 | 11/1993 | Leighton et al.. | |
| 5,364,374 | 11/1994 | Morrison et al. | 604/272 |
| 5,451,513 | 9/1995 | Maliga et al. | 435/172.3 |
| 5,457,041 | 10/1995 | Ginaven et al. | 435/172.1 |
| 5,516,670 | 5/1996 | Kuehnle et al. | 435/172.1 |
| 5,523,222 | 6/1996 | Page et al. | 435/172.3 |

OTHER PUBLICATIONS

Eriksson, et al., "In Vivo Cell Culture Accelerates Reepithelialization," *Surgical Forum* XLII:670–673 (1991).

Fynan, E.F., et al., "DNA Vaccines: Protective Immunizations by Parenteral, Mucosal, and Gene–Gun Inoculations," *Proc. Natl. Acad. Sci. USA*, 90:11478–11482 (1993).

Garlick et al., "Retrovirus–Mediated Transduction of Cultured Epidermal Keratinocytes," *Journal of Investigative Dermatology* 97:824–829 (1991).

Juni, et al, "Controlled Drug Permeation. II. Comparative Permeability and Stability of Butamben and Benzocaine," *Chem. Pharm. Bull.* 25:1098–1100 (1977).

Kaufman, et al., "Topical Oxygen and Burn Wound Healing: A Review," *Burns* 9:169–173 (1983).

LaChapelle, J.–M., et al., "Tatouages Permanents Consécutifs a des Injections par Dermo–Jet®," *Ann. Dermatol. Venereol. (Paris)*, 109:939–946 (1982) (In French, with Abstract in English).

Majumdar, A., and P. Stroeve, "Diffusion of Local Anaesthetics Through Liquid Membranes," (1986).

Marikovsky, M., et al., "Appearance of Heparin–Binding EGF–Like Growth Factor in Wound Fluid as a Response to Injury," *Proc. Natl. Acad. Sci. USA*, 90:3889–3893 (1993).

Morgan et al., "Expression of an Exogenous Growth Hormone Gene by Transplantable Human Epidermal Cells," *Science* 237:1476–1479 (1987).

Moynahan, E.J., et al., "Development of Jet Injection and Its Application to Intralesional Therapy in Dermatology," *Brit. Med. J.*, 2:1541–1543 (1965).

Read, L.C., and C. George–Nascimento, "Epidermal Growth Factor: Physiological Roles and Therapeutic Applications," *Biotech. Ther.*, 1:237–272 (1989–1990).

Rheinwald and Green, "Epidermal Keratinocytes: The Formation of Keratinizing Colonies from Single Cells," *Cell*, pp. 331–343 (1975).

Webster, R.G., et al., "Protection of Ferrets Against Influenza Challenge with a DNA Vaccine to the Haemagglutinin," *Vaccine*, 12:1495–1498 (1994).

Wilson et al., "Implantation of Vascular Grafts Lined with Genetically Modified Endothelial Cells," *Science* 244:1344–1346 (1989).

Wright, P. C., "Fundamentals of Acute Burn Care and Physical Therapy Management," *Physical Therapy* 64:1217–1231.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 4283 base pairs
        ( B ) TYPE: nucleic acid
        ( C ) STRANDEDNESS: double
        ( D ) TOPOLOGY: circular ( i i ) MOLECULE TYPE: other nucleic acid
        ( A ) DESCRIPTION: /desc ="Plasmid DNA"

( i x ) FEATURE:
        ( A ) NAME/KEY: CDS
        ( B ) LOCATION: join(713..721, 981..1250)

( x i ) SEQUENCE DESCRIPTION: SEQ ID NO:1:

```
GGGCGAATTC  GATCCTGCAG  GTCCGTTACA  TAACTTACGG  TAAATGGCCC  GCCTGGCTGA      60

CCGCCCAACG  ACCCCCGCCC  ATTGACGTCA  ATAATGACGT  ATGTTCCCAT  AGTAACGCCA     120

ATAGGGACTT  TCCATTGACG  TCAATGGGTG  GAGTATTTAC  GGTAAACTGC  CCACTTGGCA     180

GTACATCAAG  TGTATCATAT  GCCAAGTACG  CCCCCTATTG  ACGTCAATGA  CGGTAAATGG     240

CCCGCCTGGC  ATTATGCCCA  GTACATGACC  TTATGGGACT  TTCCTACTTG  GCAGTACATC     300

TACGTATTAG  TCATCGCTAT  TACCATGGTG  ATGCGGTTTT  GGCAGTACAT  CAATGGGCGT     360

GGATAGCGGT  TTGACTCACG  GGGATTTCCA  AGTCTCCACC  CCATTGACGT  CAATGGGAGT     420

TTGTTTTGGC  ACCAAAATCA  ACGGGACTTT  CCAAAATGTC  GTAACAACTC  CGCCCCATTG     480
```

```
ACGCAAATGG GCGGTAGGCG TGTACGGTGG GAGGTCTATA TAAGCAGAGC TCGTTTAGTG      540

AACCGTCAGA TCGCCTGGAG ACGCCATCCA CGCTGTTTTG ACCTCCATAG AAGACACCGG      600

GACCGATCCA GCCTCCGCGG CCGGGAACGG TGCATTGGAA CGGACTCTAG AGGATCCCAA      660

GGCCCAACTC CCCGAACCAC TCAGGGTCCT GTGGACAGCT CACCTAGCTG CA ATG         715
                                                            Met
                                                             1

GCT ACA GGTAAGCGCC CCTAAAATCC CTTTGGCACA ATGTGTCCTG AGGGGAGAGG         771
Ala Thr
CAGCGACCTG TAGATGGGAC GGGGGCACTA ACCCTCAGGG TTTGGGGTTC TGAATGTGAG      831

TATCGCCATC TAAGCCCAGT ATTTGGCCAA TCTCAGAAAG CTCCTGGCTC CCTGGAGGAT      891

GGAGAGAGAA AAACAAACAG CTCCTGGAGC AGGGAGAGTG TTGGCCTCTT GCTCTCCGGC      951

TCCCTCTGTT GCCCTCTGGT TTCTCCCCA GGC TCC CGG ACG TCC CTG CTC CTG       1004
                                 Gly Ser Arg Thr Ser Leu Leu Leu
                                  5                           10

GCT TTT GGC CTG CTC TGC CTG CCC TGG CTT CAA GAG GGC AGT GCC TTC       1052
Ala Phe Gly Leu Leu Cys Leu Pro Trp Leu Gln Glu Gly Ser Ala Phe
         15                  20                  25

CCA ACC ATT CCC TTA TAT CAA GCT TCG ATA TCC CGG GTT AAT AGT GAC       1100
Pro Thr Ile Pro Leu Tyr Gln Ala Ser Ile Ser Arg Val Asn Ser Asp
         30                  35                  40

TCT GAA TGT CCC CTG TCC CAC GAT GGG TAC TGC CTC CAT GAT GGT GTG       1148
Ser Glu Cys Pro Leu Ser His Asp Gly Tyr Cys Leu His Asp Gly Val
     45                  50                  55

TGC ATG TAT ATT GAA GCA TTG GAC AAG TAT GCA TGC AAC TGT GTT GTT       1196
Cys Met Tyr Ile Glu Ala Leu Asp Lys Tyr Ala Cys Asn Cys Val Val
 60              65                  70                      75

GGC TAC ATC GGG GAG CGA TGT CAG TAC CGA GAC CTG AAG TGG TGG GAA       1244
Gly Tyr Ile Gly Glu Arg Cys Gln Tyr Arg Asp Leu Lys Trp Trp Glu
                 80                  85                  90

CTG CGC TGAAAACACC GTGCGGCCGC ATCGATCTCG AGCATGCATC TAGAGGGCCC        1300
Leu Arg
TATTCTATAG TGTCACCTAA ATGCTAGAGC TCGCTGATCA GCCTCGACTG TGCCTTCTAG      1360

TTGCCAGCCA TCTGTTGTTT GCCCCTCCCC CGTGCCTTCC TTGACCCTGG AAGGTGCCAC      1420

TCCCACTGTC CTTTCCTAAT AAAATGAGGA AATTGCATCG CATTGTCTGA GTAGGTGTCA      1480

TTCTATTCTG GGGGTGGGG TGGGCAGGA CAGCAAGGGG GAGGATTGGG AAGACAATAG       1540

CAGGCATGCT GGGGATGCGG TGGGCTCTAT GGAACCAGCT GGGGCTCGAG CATGCAAGCT      1600

TGAGTATTCT ATAGTGTCAC CTAAATAGCT TGGCGTAATC ATGGTCATAG CTGTTTCCTG      1660

TGTGAAATTG TTATCCGCTC ACAATTCCAC ACAACATACG AGCCGGAAGC ATAAAGTGTA      1720

AAGCCTGGGG TGCCTAATGA GTGAGCTAAC TCACATTAAT TGCGTTGCGC TCACTGCCCG      1780

CTTTCCAGTC GGGAAACCTG TCGTGCCAGC TGCATTAATG AATCGGCCAA CGCGCGGGA      1840

GAGGCGGTTT GCGTATTGGG CGCTCTTCCG CTTCCTCGCT CACTGACTCG CTGCGCTCGG      1900

TCGTTCGGCT GCGGCGAGCG GTATCAGCTC ACTCAAAGGC GGTAATACGG TTATCCACAG      1960

AATCAGGGGA TAACGCAGGA AGAACATGTG AGCAAAAGG CCAGCAAAAG GCCAGGAACC       2020

GTAAAAAGGC CGCGTTGCTG GCGTTTTTCG ATAGGCTCCG CCCCCCTGAC GAGCATCACA      2080

AAAATCGACG CTCAAGTCAG AGGTGGCGAA ACCCGACAGG ACTATAAAGA TACCAGGCGT      2140

TTCCCCCTGG AAGCTCCCTC GTGCGCTCTC CTGTTCCGAC CCTGCCGCTT ACCGGATACC      2200

TGTCCGCCTT TCTCCCTTCG GGAAGCGTGG CGCTTTCTCA TAGCTCACGC TGTAGGTATC      2260

TCAGTTCGGT GTAGGTCGTT CGCTCCAAGC TGGGCTGTGT GCACGAACCC CCCGTTCAGC      2320
```

-continued

| | | | | | |
|---|---|---|---|---|---|
| CCGACCGCTG | CGCCTTATCC | GGTAACTATC | GTCTTGAGTC | CAACCCGGTA | AGACACGACT | 2380 |
| TATCGCCACT | GGCAGCAGCC | ACTGGTAACA | GGATTAGCAG | AGCGAGGTAT | GTAGGCGGTG | 2440 |
| CTACAGAGTT | CTTGAAGTGG | TGGCCTAACT | ACGGCTACAC | TAGAAGGACA | GTATTTGGTA | 2500 |
| TCTGCGCTCT | GCTGAAGCCA | GTTACCTTCG | GAAAAGAGT | TGGTAGCTCT | TGATCCGGCA | 2560 |
| AACAAACCAC | CGCTGGTAGC | GGTGGTTTTT | TTGTTTGCAA | GCAGCAGATT | ACGCGCAGAA | 2620 |
| AAAAAGGATC | TCAAGAAGAT | CCTTTGATCT | TTTCTACGGG | GTCTGACGCT | CAGTGGAACG | 2680 |
| AAAACTCACG | TTAAGGGATT | TTGGTCATGA | GATTATCAAA | AAGGATCTTC | ACCTAGATCC | 2740 |
| TTTTAAATTA | AAAATGAAGT | TTTAAATCAA | TCTAAAGTAT | ATATGAGTAA | ACTTGGTCTG | 2800 |
| ACAGTTACCA | ATGCTTAATC | AGTGAGGCAC | CTATCTCAGC | GATCTGTCTA | TTTCGTTCAT | 2860 |
| CCATAGTTGC | CTGACTCCCC | GTCGTGTAGA | TAACTACGAT | ACGGGAGGGC | TTACCATCTG | 2920 |
| GCCCCAGTGC | TGCAATGATA | CCGCGAGACC | CACGCTCACC | GGCTCCAGAT | TTATCAGCAA | 2980 |
| TAAACCAGCC | AGCCGGAAGG | GCCGAGCGCA | GAAGTGGTCC | TGCAACTTTA | TCCGCCTCCA | 3040 |
| TCCAGTCTAT | TAATTGTTGC | CGGGAAGCTA | GAGTAAGTAG | TTCGCCAGTT | AATAGTTTGC | 3100 |
| GCAACGTTGT | TGGCATTGCT | ACAGGCATCG | TGGTGTCACG | CTCGTCGTTT | GGTATGGCTT | 3160 |
| CATTCAGCTC | CGGTTCCCAA | CGATCAAGGC | GAGTTACATG | ATCCCCCATG | TTGTGCAAAA | 3220 |
| AAGCGGTTAG | CTCCTTCGGT | CCTCCGATCG | TTGTCAGAAG | TAAGTTGGCC | GCAGTGTTAT | 3280 |
| CACTCATGGT | TATGGCAGCA | CTGCATAATT | CTCTTACTGT | CATGCCATCC | GTAAGATGCT | 3340 |
| TTTCTGTGAC | TGGTGAGTAC | TCAACCAAGT | CATTCTGAGA | ATAGTGTATG | CGGCGACCGA | 3400 |
| GTTGCTCTTG | CCCGGCGTCA | ATACGGGATA | ATACCGCGCC | ACATAGCAGA | ACTTTAAAAG | 3460 |
| TGCTCATCAT | TGGAAAACGT | TCTTCGGGGC | GAAAACTCTC | AAGGATCTTA | CCGCTGTTGA | 3520 |
| GATCCAGTTC | GATGTAACCC | ACTCGTGCAC | CCAACTGATC | TTCAGCATCT | TTTACTTTCA | 3580 |
| CCAGCGTTTC | TGGGTGAGCA | AAAACAGGAA | GGCAAAATGC | CGCAAAAAAG | GGAATAAGGG | 3640 |
| CGACACGGAA | ATGTTGAATA | CTCATACTCT | TCCTTTTTCA | ATATTATTGA | AGCATTTATC | 3700 |
| AGGGTTATTG | TCTCATGAGC | GGATACATAT | TTGAATGTAT | TTAGAAAAAT | AAACAAATAG | 3760 |
| GGGTTCCGCG | CACATTTCCC | CGAAAAGTGC | CACCTGACGT | CTAAGAAACC | ATTATTATCA | 3820 |
| TGACATTAAC | CTATAAAAAT | AGGCGTATCA | CGAGGCCCTT | TCGTCTCGCG | CGTTTCGGTG | 3880 |
| ATGACGGTGA | AAACCTCTGA | CACATGCAGC | TCCCGGAGAC | GGTCACAGCT | TGTCTGTAAG | 3940 |
| CGGATGCCGG | GAGCAGACAA | GCCCGTCAGG | GCGCGTCAGC | GGGTGTTGGC | GGGTGTCGGG | 4000 |
| GCTGGCTTAA | CTATGCGGCA | TCAGAGCAGA | TTGTACTGAG | AGTGCACCAT | ATGCGGTGTG | 4060 |
| AAATACCGCA | CAGATGCGTA | AGGAGAAAAT | ACCGCATCAG | GCGCCATTCG | CCATTCAGGC | 4120 |
| TGCGCAACTG | TTGGGAAGGG | CGATCGGTGC | GGGCCTCTTC | GCTATTACGC | CAGCTGGCGA | 4180 |
| AAGGGGGATG | TGCTGCAAGG | CGATTAAGTT | GGGTAACGCC | AGGGTTTTCC | CAGTCACGAC | 4240 |
| GTTGTAAAAC | GACGGCCAGT | GAATTGTAAT | ACGACTCACT | ATA | | 4283 |

( 2 ) INFORMATION FOR SEQ ID NO:2:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Thr | Gly | Ser | Arg | Thr | Ser | Leu | Leu | Leu | Ala | Phe | Gly | Leu | Leu |
|---|---|---|---|---|---|---|---|---|---|---|---|---|---|---|---|
| 1 | | | | 5 | | | | | 10 | | | | | 15 | |

| | | | | | | | | | | | | | | |
|---|---|---|---|---|---|---|---|---|---|---|---|---|---|---|
| Cys | Leu | Pro | Trp<br>20 | Leu | Gln | Glu | Gly | Ser<br>25 | Ala | Phe | Pro | Thr | Ile<br>30 | Pro | Leu |
| Tyr | Gln | Ala<br>35 | Ser | Ile | Ser | Arg | Val<br>40 | Asn | Ser | Asp | Ser | Glu<br>45 | Cys | Pro | Leu |
| Ser | His<br>50 | Asp | Gly | Tyr | Cys | Leu<br>55 | His | Asp | Gly | Val | Cys<br>60 | Met | Tyr | Ile | Glu |
| Ala | Leu | Asp | Lys | Tyr | Ala<br>70 | Cys | Asn | Cys | Val | Val<br>75 | Gly | Tyr | Ile | Gly | Glu<br>80 |
| Arg | Cys | Gln | Tyr | Arg<br>85 | Asp | Leu | Lys | Trp | Trp<br>90 | Glu | Leu | Arg | | | |

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PCR Primer"

( x i ) SEQUENCE DESCRIPTION: SEQ ID NO:3:

TCAATAGTGA CTCTGAATGT CCCC        24

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PCR Primer"

( x i ) SEQUENCE DESCRIPTION: SEQ ID NO:4:

GGCTGATCAG CGAGCTCTAG        20

GENE DELIVERY BY MICRONEEDLE INJECTION

CROSS-REFERENCE TO RELATED APPLICATIONS

This is a continuation-in-part of U.S. Ser. No. 08/076,550, filed Jun. 11, 1993, now abandoned, which is a continuation-in-part of U.S. Ser. No. 07/897,357, filed Jun. 11, 1992, for "System and Method for Transplantation of Cells", by Elof Eriksson and Peter M. Vogt, now U.S. Pat. No. 5,423,778, which is a continuation-in-part of U.S. Ser. No. 07/707,248, filed May 22, 1991, by Elof Eriksson, now U.S. Pat. No. 5,152,757, which is a continuation of U.S. Ser. No. 07/451,957 filed Dec. 14, 1989, now abandoned.

FIELD OF THE INVENTION

The invention relates to a system for delivering genetic material into cells in situ in a patient.

BACKGROUND OF THE INVENTION

Various methods for introducing genetic material into an internal or external target site on an animal exist. Most prominent are methods of accelerated particle mediated gene transfer, such as are described in U.S. Pat. Nos. 4,945,050 (Sanford, et al.), 5,204,253 (Sanford, et al.) and 5,015,580 (Christou, et al.).

Other methods have focussed on introducing genetic material into skin cells, particularly keratinocytes. Keratinocytes are the principle cells which cover the surface of the body. They are capable of producing proteins, particularly keratin, which constitute the main surface barriers of the body. For several different reasons, keratinocytes are attractive potential targets for gene transfer. Since they are located on the surface of the body, they are easily accessed both for gene manipulation and monitoring. If complications from gene transfer would occur, for instance, the development of local tumors or local infections, these could more easily be treated in the skin than elsewhere.

To date, genetic manipulation of keratinocytes has been done in one principal way. Skin has been harvested, the keratinocytes have been separated from the fibroblasts, and then the keratinocytes individually isolated and brought into suspension. These suspensions of keratinocytes have then been cultured to confluence using tissue culture techniques, as reported by Rheinwald, J. G., Green, H. Serial Cultivation of Human Epidermal Keratinocytes: The Formation of Keratinizing Colonies From Cells. *Cell* G, 331–343, 1975.

The new genetic material has been introduced into the keratinocyte while being grown in vitro using either a viral vector or plasmid, as reported by Morgan, J. R., Barrandon, Y., Green, H., Mulligan, R. C. Expression of an Exogenous Growth Hormone Glue by Transplantable Human Epidermal Cells. *Science*, Vol. 237, 1476–1479 (1987) and Tenmer, J., Lindahl, A., Green, H. Human Growth Hormone in the Blood of Athymic Mice Grafted With Cultures of Hormone-Secreting Human Keratinocytes. *FASEB J.*, 4:3245–3250 (1990). The transfected cells are then usually resuspended and grown on selective media in order to increase the yield of transfection. Sheets of keratinocytes are then transplanted back to the mammal from which the keratinocytes were harvested.

Even though the in vitro yield has been acceptable, the in vivo yield has been unacceptably low, both short and long term. It has been very difficult to document any significant long term (more than thirty days) expression with these techniques, for example, as reported by Garlick, J. A., Katz, A. B., Fenvjes Esitaichman, L. B. Retrovirus Mediated Transduction of Cultured Epidermal Keratinocytes. *J. Invest. Dermatol.*, 97:824–829, 1991.

SUMMARY OF THE INVENTION

Direct gene transfer of genetic material into internal or external target sites in optional combination with the use of an "in vivo" culture chamber is particularly effective for long term expression of polypeptides.

Direct delivery of genetic material is accomplished by repetitive microneedle injection into intact skin cells, open skin wounds, and internal tissues or organs. In a 1 $cm^2$ target area, microneedles make between 500 and 5000 separate injections of an aqueous solution comprising genetic material at a desired concentration.

By employing the optional culture chamber system, direct in vivo gene transfer to exposed cells in an open wound can be performed. If these cells were not covered by the chamber, they would desiccate and die. The chamber also completely seals the wound from the outside, eliminating the spread of genetic material and vectors to places outside of the wound. At the same time, the chamber prevents the accidental introduction of undesired contamination, including viruses and other microorganisms and chemical contaminants into the wound.

The use of the chamber system for gene transfer also allows non-invasive assessment of the success of transfer by assaying for the presence of the expressed protein in wound fluid, in contrast to the prior art use of invasive techniques, such as biopsies, in order to achieve the same assessment of early expression.

A wide variety of proteins and materials can be expressed, either for secretion into the general blood and lymphatic system, or to alter the properties of the protein, for example, to not express proteins eliciting an immune response against the transplanted cell.

It is an object of the present invention to provide a method for delivery of genetic material which is economical, and practical, and can be customized to the patient with minimal effort and expense.

It is another object of the present invention to provide an apparatus suitable for direct delivery of genetic material to internal target sites.

DETAILED DESCRIPTION OF THE INVENTION

Figure 1:
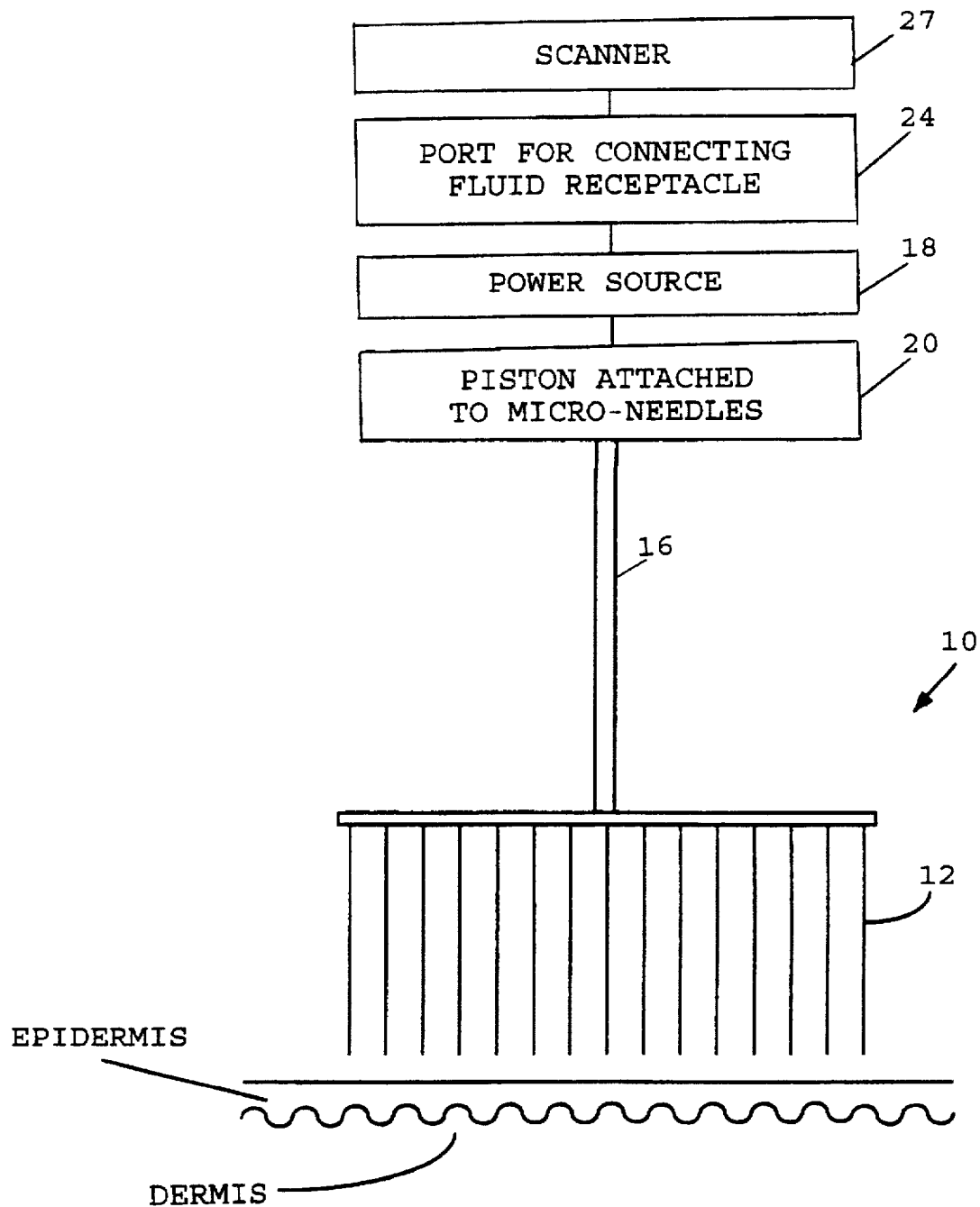
FIG. 1 is a schematic representation of a microseeding device for delivering genetic material into cells of a patient.

The method described herein is a method for delivering genetic material into cells at an internal or external target site on an human or non-human patient using a microneedle delivery apparatus. This process has been termed "microseeding" by the inventors. Examples of disorders that can be treated include wounds such as burns, pain, tumors, and infections.

Also described herein is a microneedle delivery apparatus for delivering DNA according to the method of the present invention.

Also described herein is use of a treatment system for wounds and other skin disorders that can optionally be employed in the method of the present invention when delivering DNA to an external target site. The treatment system has previously been described in U.S. Pat. No. 5,152,757, which is incorporated herein by reference.

Target Cells

The method of the present invention delivers genetic material into any accessible target cell type in any human or non-human patient. Among non-human patients, most preferred are mammalian animals, especially domesticated animals such as dogs, cats, cattle, swine, goats, sheep and the like, in which the method is envisioned as a desired veterinary therapy.

The preferred target cells in all target animals are skin cells, which are most readily transduced with genetic material because of their proximity to the exterior of the patient. "Skin" is intended to encompass cells in all skin layers including epidermal, dermal, and subdermal layers. More specifically, skin includes superficial keratinocytes, stem cell keratinocytes and dermal fibroblasts. For purposes of this patent application, "skin" also encompasses the muscular tissue beneath the skin that can be accessed from the exterior by the microneedles described herein. The target skin can be intact or can be prepared for treatment by wounding. In addition, internal tissues and organs within a patient are also desirable target sites into which exogenous genetic material can be introduced in keeping with the method. Suitable internal sites include any soft tissue that can be pierced by microneedles as described herein. For purposes of this patent application, "internal sites" are those target sites which are not accessible from the exterior of the patient but which are accessible using the microneedle delivery device for internal use, as disclosed herein. Without intending to limit application of the method to particular internal sites, specifically envisioned as targets are smooth and striated muscle, connective and epithelial tissues, walls of abdominal passages, and internal organs including, but not limited to, liver, kidney, stomach, appendix, intestines, pancreas, lungs, heart, bladder, gall bladder, brain and other nervous system cells, as well as reproductive, endocrine, lymphatic and other glandular tissues.

In any particular target tissue, it is envisioned that a subpopulation of cells (e.g., keratinocytes in skin cells) may be most preferred target cells, insofar as they exhibit a superior ability to take up or express introduced genetic material. The particular preferred subpopulations can readily be determined empirically in an experimental system designed to measure a particular response to introduction of a particular genetic molecule. If a particular subpopulation of cells is found to be a preferred target, one of ordinary skill will understand how to direct the genetic material into that subpopulation either by orienting the microneedle delivery apparatus toward a portion of a target tissue, or by selecting a preferred delivery depth to which the genetic material is delivered, or both.

Genetic Material

The genetic material that is introduced into the target cells using the method can be any native or non-native genetic molecule that can provide a desirable activity to a target cells. The genetic material can encode any native or non-native protein or polypeptide having such a desirable activity in a target cell. Alternatively, the introduction of the genetic material itself can alter the target in a desirable way, such as by interference with the transcription or translation of a gene normally present in the target. "Non-native" means that neither the genetic material, nor any protein or polypeptide product encoded by the genetic material is detectable in the untreated target cells or tissue. The nature of the introduced genetic material itself forms no part of the present invention.

The genetic material, can be RNA, but is preferably DNA and is most preferably supercoiled plasmid DNA. The genetic material is prepared according to any standard preparation or purification method among the many known to the art and is provided in an aqueous solution, buffered or unbuffered. The amount of genetic material delivered is not absolutely critical, though better results have been observed for DNA molecules tested when the amount of DNA is below 500 µg, and preferably below 200 µg. Suitable concentrations can readily be determined by routine experimentation. Delivery to the target site of approximately 100 µl of an aqueous solution containing genetic material in the preferred concentration range is sufficient to function in the method. The genetic material can be attached to microparticles such as iron oxide particles in the range of 0.5 to 1 micron in size. Alternatively, unsupported genetic material in solution is also suitable for delivery according to the method.

The genetic material typically includes an expressible DNA sequence that encodes a native or non-native polypeptide. The DNA can be of any length and can include genomic DNA fragments, engineered DNA produced in a microbial host, or synthetic DNA produced according to known chemical synthetic methods, including, but not limited to, the Polymerase Chain Reaction. The art is cognizant of the various required and preferred elements (including promoters, terminators, transcription- and translation-regulating sequences, and the like) that one of ordinary skill would provide on an expressible genetic construct. One of ordinary skill is also able to select appropriate elements from the many known elements to facilitate or optimize expression in a particular target animal. The native or non-native polypeptide produced in the method can be maintained intracellularly or secreted to the extracellular space. One of ordinary skill in the art is familiar with the genetic elements necessary to direct a sequence to a particular cellular or extracellular microenvironment and with methods for constructing a genetic construct to facilitate such direction. For example, a polypeptide expressed after gene transfer can be directed to cross a cell membrane by adding an appropriate signal peptide to the gene that encodes the polypeptide.

Desirable proteins that can be expressed after gene transfer include, without limitation, growth factors, hormones, and other therapeutic proteins. These would speed the healing of wounds and correct certain deficiencies, such as parathyroid, growth hormone, and other hormone deficiencies, as well as deficiencies of certain clotting factors such as factor VIII. For instance, if the gene encoding the growth factor is introduced into the genome or cytoplasm of target skin cells in a wound, these cells can be made to produce a desirable growth factor. The expressed growth factor will then not only speed the healing of the wound, but may also help to heal wounds that would not heal otherwise.

Cells can also be engineered to not express a protein, such as a protein involved in an immune response, for example, a human leukocyte antigen (HLA). This can be accomplished in a variety of understood ways, the most common being the introduction of "antisense" genetic material that hybridizes with mRNA present in a cell to prevent translation of the mRNA.

This approach can be used to insert other genetic material of interest into target cells in order to eliminate, or restore, missing or defective functions of patients having any of a variety of skin diseases. Also, the mode in which cytokines act can be changed in that when a factor is expressed in a cell that normally does not produce that factor, a paracrine pathway can be changed into an autocrine pathway. In the same fashion, target cells can be genetically engineered to repair or compensate for inherent genetic defects, such as epidermolysis bullosa. The target cells in a superficial excisional wound can be microseeded with appropriate genetic material to generate a new epidermis with the desired features. Problematic wounds may require coverage of the defect and fast healing.

Microneedles

Figure 2:
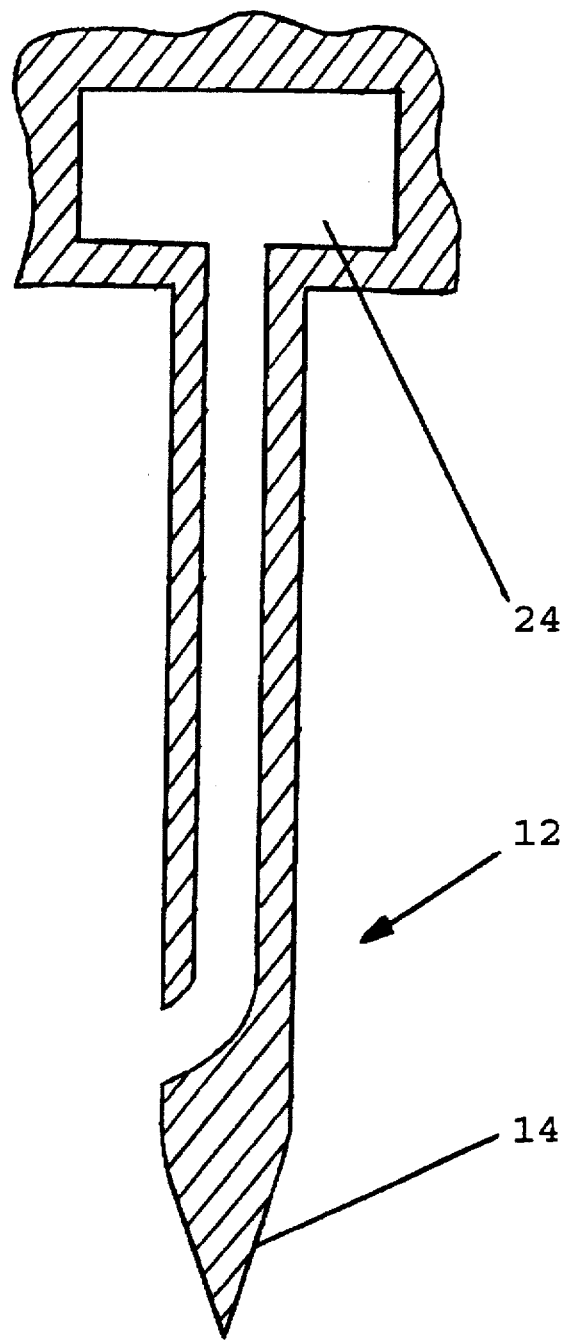
FIG. 2 is a cross-sectional view of a microneedle 10 shown in FIG. 1.
Figure 3A:
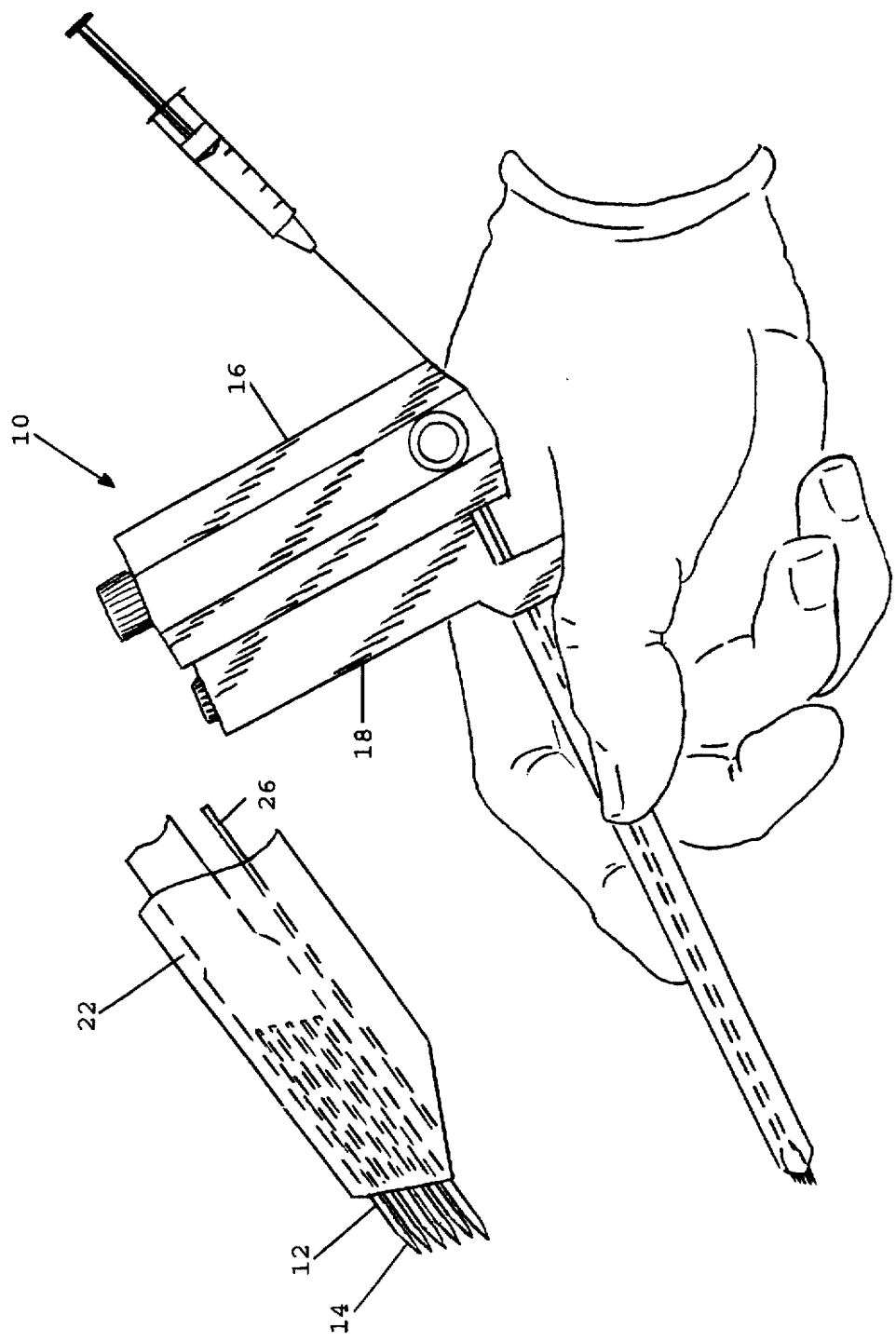
FIG. 3 (*a* and *b*) are representations of microseeding devices for delivering genetic material into cells of a patient.
Figure 3B:
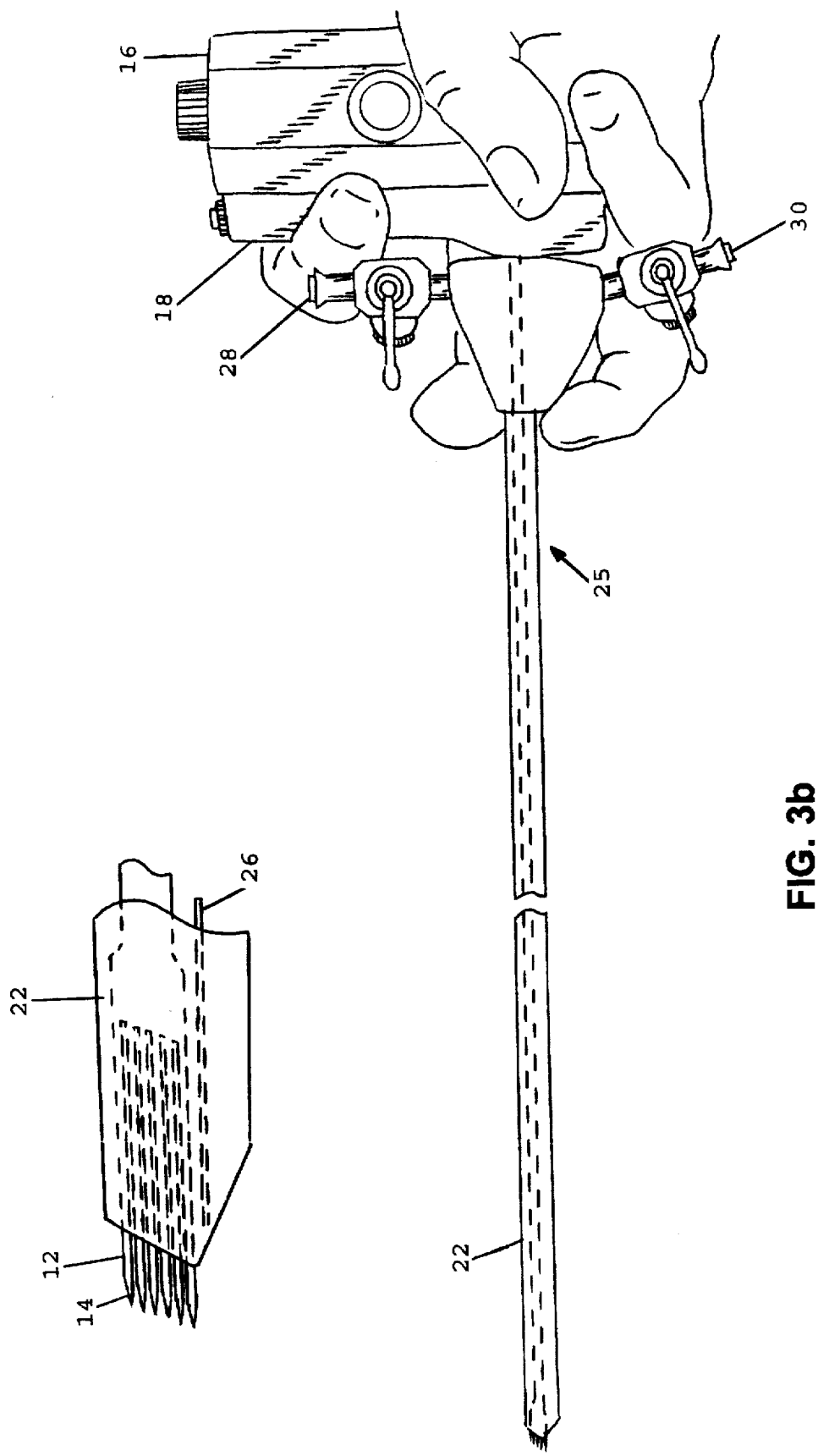

Genetic material can be delivered directly into target cells of a patient using a microneedle delivery apparatus to repeatedly puncture a target area, and to deliver, with each puncture, a small amount of the genetic material provided in an aqueous solution. A microneedle delivery device 10, suitable for use in the method of the present invention, such as the preferred devices shown in FIGS. 1-3 (a and b), include microneedles 12 having beveled tips 14, mounted in a row on a support 16, such as a handle. The microneedle diameter is about 300 microns. The beveled tip 14 tapers to a zero diameter along the 2 mm closest to the tip; at 100 microns from the tip, the diameter is about 60 microns, while at 50 microns from the tip, the diameter is about 35 microns. The beveled tip 14 facilitates puncturing of the selected target site by the microneedles 12 and opening of cells along the needle path, which is thought to facilitate high expression levels after delivery. The microneedles 12 can be solid (FIG. 3) or can have hollow centers (as in FIG. 2), although preferred microneedles are solid, since no genetic material is lost to the interior of the needle during delivery. If hollow needles are used, the hollow center should terminate to the side, rather than the bottom, of the tip 14, as is shown in FIG. 2. Moreover, the solid interior applies significantly higher force than hollow needles to the solution containing the genetic material, to help direct the material into the target cells.

The microneedles 12 are reciprocally driven by a power source 18, secured to the support, which can be an electric motor or any other suitable power source. The microneedles 12 have a proximal end and a distal end, relative to the power source 18. If the motor is electric, as in the preferred devices, the motor is attached to a switch that controls whether electric power is applied to the motor. The switch can provide variable or constant power to the device. The motor is connected by a cam to a reciprocating piston 20, which includes an attachment slot thereupon. The microneedles are joined to the piston attachment slot through a bar connected to the microneedles and inserted into the piston attachment slot. When energized, the piston can oscillate the microneedles at a wide range of speeds between 8 and 50 oscillations per second. The speed of the needles is not thought to be critical to their use in the invention. The amplitude of the oscillating microneedles can vary up to approximately 5 mm. The amplitude is also not believed to be critical, the effect of a greater amplitude simply being a deeper penetration depth. A 3 mm amplitude is suitable. Both the speed and amplitude can be predetermined by, for example, varying the power applied to the motor.

Surrounding the microneedles is a needle tube 22, shaped to accommodate the microneedles 12, which supports the microneedles 12 in all four directions and urges the microneedles 12 into a very small delivery area. The needle tube 22 itself is rigid or semi-rigid and is secured to the support 16 with a fastener, such as a wing nut, in a narrow opening.

If hollow microneedles 12 are used, as in FIG. 2 (schematic), the hollow centers of the microneedles are in fluid communication with controllable port 24 for connecting a fluid receptacle that holds the solution comprising the genetic material. The fluid receptacle can be a syringe. The solution can flow from the fluid receptacle through the hollow centers to the distal tips 14 of the microneedles 12.

If solid microneedles are used, delivery of the solution comprising genetic material through the microneedles to the tips is not practical. No fluid delivery structure is needed if the device is to be used for delivery only to an external target site, such as an intact skin or wound target site because fluid delivery can be readily accomplished by manual delivery of the solution to the site before applying the microneedle device. However, tubing for delivering the genetic material, as described elsewhere herein, is preferably also used for delivery to an external target site because less DNA is consumed when delivery is performed through delivery tubing.

When the genetic material is to be injected into internal sites within the patient, the genetic material needs to be delivered to the distal tips 14 of the microneedles 12. In a preferred apparatus 25 that facilitates direct gene transfer to an internal or external target site, separate structures are provided as part of the device, to bring the genetic material in solution to the distal tips of the solid microneedles. As shown in both embodiments of FIGS. 3a and 3b, the tube that surrounds the needle can be provided with one or more additional channels 26 on its inner or outer surface to serve as fluid conduits. The channels 26 can be separate from and attached to the needle tube, or can be formed directly thereto or therein. A first channel terminates at a first end at the motor end of the device at a controllable port 28 connectable to a fluid receptacle such as a syringe. A second end of the channel is at the distal end of the microneedles 12. A second, optional, larger channel, connectable by a controllable port 30 at one end to an external suction device, also opens at the opposite end near the tips, and provides suction of fluid from the delivery site. The second channel can alternatively be provided with a second fluid receptacle and used as a second fluid delivery channel to deliver a second fluid, such as a sealant, a biological glue or a hemostatic agent, to the distal ends of the solid microneedle tips.

The overall size of the apparatus 25, and, in particular the length of the microneedle 12, is such that that power source remains user-operable and external to the patient when the distal end of the microneedle 12 is positioned at the internal target site. Thus, the length will depend upon the distance of the internal site from the incision through which the apparatus 25 is introduced into the patient. A suitable length of the device for internal use is 10–15 inches, preferably 13 inches, which allows adequate manipulation to numerous internal target sites.

The inventors have determined that optionally placing the microneedles 12 in a 35% (12.1M) solution of hydrochloric acid for 12 hours before use in the method etches the needles slightly. Another way to modify the needles is to bombard the needles with aluminum oxide microbeads. It is not yet known whether needle surface modification provides additional surface area onto which the genetic material can adhere during delivery, or whether the modified needle surface advantageously affects the needle's ability to puncture the cells. Although not essential, dipping the microneedle tips 14 into hot paraffin can also prevent DNA from sticking irreversibly to the microneedles during microseeding.

Direct in situ Introduction of the Genetic Material into Target Cells

Microseeding can be used to insert genetic material directly into target cells in situ in a human or non-human patient. One or more microneedles are ideal for this purpose. In the method, a solution containing genetic material is placed on the target surface. The microneedles are then moved as a group across the target site to "inject" and thereby deliver the genetic material through the surface of the target to the underlying tissue along several parallel lines. The microneedle or microneedles repeatedly penetrate a site on a surface of the target tissue to a depth within the tissue at which a plurality of preferred or most preferred target cells are found. The penetrating and delivering steps are repeated in the vicinity of the target cells until sufficient genetic material has been delivered that a change in the patient attributable to the delivery of the genetic material is detectable, preferably within twenty-four hours. The change can be physiological, biochemical, histological, genetic, or immunological, or otherwise. Detection of an added or eliminated characteristic of the patient, genetic or phenotypic, is sufficient.

The method can be used to deliver unsupported genetic material in solution, or genetic material attached to carriers, such as iron oxide microparticles. This technique is useful for delivery of a suspension of genetic material alone, without delivery of infectious viral material or attachment to microparticles. This is desirable because of the minimal sample preparation time required. In addition to persistent expression, high transient expression levels are observed.

It is preferred that a large number of independent microneedle penetrations be performed to ensure delivery of an adequate amount of genetic material in the method. The number of penetrations should range from between about 500 to about 5,000 per cm² of surface at the target site. Preferably, between 3,000 and 4,000 independent penetrations should be performed at each 1 cm² site. To reduce the total delivery time, it is highly preferred that more than one oscillating microneedle, preferably six or more oscillating microneedles, be used to deliver the genetic material. Because of the large number of microinjections, it is also highly preferred that the oscillation be accomplished using an apparatus designed for repeated penetration of oscillating microneedles, such as either of the microneedle delivery devices described herein. Such a microneedle delivery device, placed under control of a scanner 27, can systematically and accurately cover a predefined area of skin or other tissue, and can deposit the genetic material very evenly into a large number of target cells in the predefined area.

Figure 4:
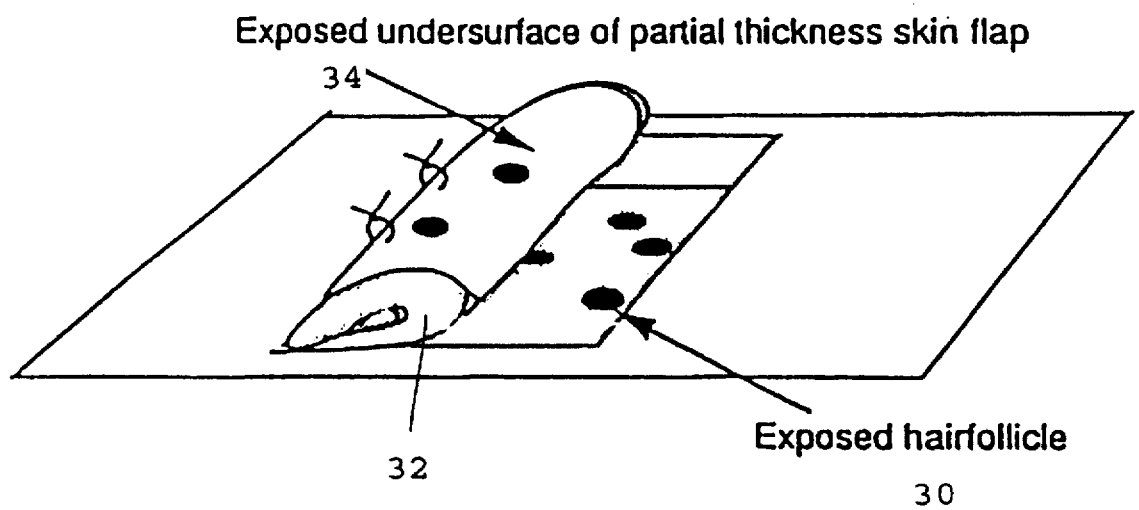
FIG. 4 is a schematic of the exposed undersurface of a partial thickness skin flap used to expose hair follicles to obtain epidermal stem cells.

For delivery into a wound or intact skin, the microneedles are placed over a desired treatment site that has previously been prepared, as needed. No particular preparation is necessary for delivery into intact skin. The site for delivery of genetic material into a wound is prepared by removing infected or burned skin, if necessary, or by creating an appropriate wound for the purpose of in situ delivery of genetic material. An artificially created wound is shown in FIG. 4. Stem cells located in the hair follicles 30 deep to the epidermal dermal junction can be exposed by creating a flap 32 of epidermis where the deep portion of the flap contains the basal layer of the epidermis. The exposed wound surface 34 contains the portion of the hair follicles with the stem cell keratinocytes. After delivery of the genetic material, the epidermal flap 32 of an intentional wound is sutured back in place and the wound is sealed with a dressing or in a chamber, as described below.

When internal delivery is desired, surgical access to a desired delivery site is provided for a microseeding apparatus such as that described herein. Surgical access to the interior of the patient can be provided through laparoscopic ports made in a manner known to the art. The laparoscopic ports can also accommodate a viewing scope and an assisting instrument for accurate placement of the microseeding apparatus. In such cases, no wound chamber is needed after treatment, since the treated cells are not exposed to the air and will not dry out.

Regardless of location of the delivery site, the beveled tips of a plurality of microneedles are surrounded with an aqueous solution comprising the genetic material. As noted above, the genetic material is provided to the microneedle tips manually or via a channel provided on the microneedle delivery device. Oscillation of the microneedles placed on the target site at a rate of between 8 and 50 oscillations per second is initiated by energizing the power source. The power source reciprocates the piston at a predetermined rate so that the microneedles repeatedly enter the treatment site to a desired depth. The desired depth, which can range from 0 to about 5 mm, is selected to deliver the solution containing genetic material to a depth at which a large number of cells competent to take up and express the genetic material are found. For instance, it has been determined by the inventors that, when the target is skin, the preferred target cells are keratinocytes, generally located at about 2 mm beneath the skin surface. The optimal penetration depth for other delivery sites can readily be determined empirically by looking under controlled experimental conditions for a desired change in an art-accepted model system, for example, a pig, using a physiological, biochemical, chemical, histological, genetic, immunological or like detection method.

After treatment, no particular method steps need to be followed. However, should one desire to either regulate the fluid in which the treatment site is bathed, or to analyze the products produced at the treatment site, isolation of the site in a vinyl adhesive chamber, or other such isolating chamber is recommended.

The technique can also be enhanced by practicing it in combination with other biological agents, such as liposomes.

This method of introducing genetic material into cells may be superior to gene transduction using plasmids or retroviral vectors, because the latter have an unacceptably low yield. Transfer of genetic material with accelerated particles, employing "gene guns," have a higher yield than plasmid or retrovital transduction, but can, in some embodiments, have other disadvantages, such as a very loud blast and a risk of accidental discharge. Moreover, this method does not leave particles inside patients after treatment. For internal delivery, the microneedles are advantageous because it is not necessary to fully expose internal organs before delivery; rather, only an few incisions large enough to receive a manipulable microneedle apparatus, assisting tool, and viewing scope are made.

Thus, microseeding of genetic material into cells with oscillating microneedles provides a practical, affordable, and a predictable method of insertion of genetic material for localized or systemic expression. The invention finds particular utility as a method for immunization against a non-native polypeptide, and as a method for introducing a foreign genetic material as a therapeutic agent.

The Chamber

If a polypeptide is secreted from treated intact skin or wound cells, it may be desirable to localize the secreted polypeptide at or near the target site. Such is the case, for example, when the secreted polypeptide accelerates wound healing. In such cases, the target site can be isolated after treatment by enclosing the treated wound site in a sealed chamber, in the manner of U.S. Pat. No. 5,152,757, which is incorporated herein by reference. The structure of the chamber is described in the referenced patent, and is not described in detail herein.

Isolation of the treatment site has an additional benefit of protecting the treatment site from external pathogens such as bacteria and viruses. Moreover, one has the ability to surround the treated target site with fluid having a desired composition, and the ability to analyze samples of the fluid to evaluate the concentrations of desired or undesired compounds in the fluid. However, if delivery is made into a non-wound skin site, use of the sealed chamber may not be necessary, as the skin provides sufficient protection to transduced cells.

In a preferred embodiment, treated skin and wound cells are protected by a system including a chamber, treatment fluid (which may be nutrient media, physiological saline, or some other compatible solution), treatment additives (such as antibiotics and buffering agents), means for controlling treatment variables and means for monitoring cell growth.

The treatment system includes a chamber securable about the periphery of a wound, having portal means for introduction into and removal of treatment fluids from the chamber, treatment fluid, at least one treatment additive, control means for treatment variables, and monitoring means for monitoring wound conditions. The chamber is secured about the periphery of a wound, a treatment fluid and at least one treatment additive are introduced into the chamber, and the treatment variables are controlled according to wound conditions.

The wound chamber, which is made of vinyl or other flexible transparent material, such as polyurethane, has a bellows shape and an opening which corresponds to the size of the wound, either the chronic wound or a superficial wound created specifically for the purpose of gene transfer. The chamber contains a small amount of normal saline with antimicrobial agents. When the microneedle is used, the DNA is delivered into the cell and the chamber with normal saline and antibiotics is then attached to the perimeter of the wound. Wound fluid is sampled in order to assay expression of the secretable gene product (e.g., growth factor) at 24 and 48 hours. The wound is treated in the chamber until healed.

The chamber encloses a predetermined surface area about the treatment site. The chamber provides protection for the wound from the surrounding non-sterile environment, control of treatment variables, containment for continuous fluid treatment, an effective delivery system for additives, direct monitoring of cell growth. Monitoring can be accomplished visually if the chamber is formed of a transparent material, or by extraction and analysis of fluid from the chamber. Fluid extracted from the system can be analyzed for factors which provide an indication of the status of healing, as well as the presence of undesirable components such as microorganisms, low oxygen, high carbon dioxide and adverse pH. The fluid may be tested for the number and type of bacteria and other microorganisms, the number and type of cells, the amount and type of proteins secreted by the patient and the cells within the chamber, and other factors such as drug levels, oxygen, carbon dioxide and pH.

The treatment system provides control over variables including temperature, specific ion concentration, colloid osmotic pressure, glucose concentration, amino acid content, fat concentration, oxygen concentration and carbon dioxide concentration and pH.

Portal means provide access for the introduction of treatment fluids and treatment additives into the chamber and extraction of fluid from the chamber. In some embodiments, treatment fluid is introduced into the chamber by injection with a conventional hypodermic syringe through the wall of the chamber, preferably made of a flexible, self-repairing plastic. In other embodiments, the chamber has an inlet and outlet port or separate inlet and outlet ports. Valve mechanisms are necessary where the apparatus is not to be connected to a treatment fluid reservoir and a drain or connected to a continuous perfusion system. The seals of the ports would be broken at an appropriate time for connection to other apparatus, such as a continuous perfusion system, at a hospital for example.

A preferred embodiment of the treatment system incorporates continuous perfusion of treatment fluid through inlet and outlet ports. A pump or gravity may be used to move the treatment fluid. The treatment fluid may be recirculated after filtering and other appropriate action (eg. heating or cooling). Alternately, fresh treatment fluid may be introduced and contaminated fluid disposed of. In an embodiment described in U.S. Pat. No. 5,152,757, the chamber contains a reservoir or more than one chamber, with the additional chamber serving as a source of fresh culture media, oxygen, and treatment additives.

As those skilled in the art will readily recognize, a removable sheet for protecting the adhesive and maintaining the sterility of the interior of the chamber is desirable. The chambers may be stored in a sterile pack for years. This chamber can take many shapes in order to fit wounds from the size of one square centimeter up to the size of a whole extremity. It is important that the adhesive surface be sufficient to secure the bandage to the skin surface to ensure a leak-proof seal.

As previously mentioned, treatment fluid and treatment additive introduction and subsequent extraction may be accomplished directly through the chamber walls by a needle and syringe. A self-repairing material to construct chamber 10 is contemplated. An alternative method would be to use inlet and outlet ports allowing the introduction and extraction of various substances into the chamber.

If the chamber is to be used to cover a wound or intact skin site, the skin adjacent to the site is cleaned so that there will be good adhesion between the chamber and the skin. The open portion of the chamber is then placed over the site, with the adhesive edges securing the chamber to the skin, then an appropriate culture medium and cells are introduced into the sealed chamber. The treatment fluid may be introduced and then extracted in favor of fresh culture media in a continuous or batch process. Selected treatment additives may be introduced into the chamber continuously or at a predetermined time or at periodic intervals. Appropriate control of treatment variables is also effected. Monitoring is accomplished by examination of the patient and visual examination of the fluid within the chamber and the wound itself. In addition, samples of fluid are extracted from the chamber for analysis and diagnosis. The chamber is removed once sufficient healing of the wound has occurred.

For example, to determine whether or not the wound is healed, the protein content of the extracted fluid is analyzed. When the protein content of the extracted fluid decreases to the level present in chambers containing fluid that are placed over normal skin, the wound is healed. Methods for determining protein content are well known in the art and are inexpensive and fast. The types of protein and the relative amounts of the types of protein can also be determined to further evaluate healing and expression of exogenous genetic material.

Control of Treatment or Culture Variables Using Wound Chamber

Treatment of each patient is specific for the conditions within the chamber. Control over treatment variables can include continuous cooling to 34° C. for the first 24 hours. Monitoring can include analyzing extracted fluid for protein and microorganisms, with samples extracted every 24 hours. For example, when the number of microorganisms is less than $10^4$ per milliliter or per cc, infection has been resolved. Protein levels checked every day should be less than 24 mg/dl/cm$^2$.

As noted above, there are a number of treatment variables which may be controlled by the system. One such treatment variable which may be controlled is temperature. It has been found that heating the wound from a temperature of approximately 27° C. (a common temperature of a lower extremity wound) to 37° C. accelerates wound healing. Experimental data has shown that at a wound temperature of approximately 37° C., the rate of wound healing is more than twice as fast as at a temperature of 27° C. The temperature of the wound area can be achieved by heating the treatment fluid. Cooling has also been proven beneficial in the case of acute burn and other traumatic wounds. Cooling reduces pain, swelling and destruction of tissue. In general terms, acute wounds benefit from cooling during the first hours after occurrence of the wound and later, wounds benefit from a temperature of approximately 7° C. Cooling can similarly be effected by cooling the treatment fluid.

Other treatment variables may also be optimized. For example, ion concentrations should be kept close to extracellular ion levels. Glucose, amino acid and fat concentrations should be kept close to the concentrations present in plasma or corresponding to a skin tissue culture medium. Oxygen and carbon dioxide concentrations should also be maintained at their normal tissue levels. Oxygen is an important treatment additive, and is essential for cell growth.

Treatment Additives and Culture Media in Wound Chamber

Normal or physiological buffered saline is the basic culture media. Buffering agents, anesthetics such as lidocaine, antibiotics such as penicillin or streptomycin, chemotherapeutic agents, and growth factors including epidermal growth factor (EGF), platelet-derived growth factor (PDGF), insulin-like growth factor (IGF), basic fibroblast growth factor (bFGF), and cholera toxin (CT) can be added to the culture/treatment media. Tissue culture mediums and fluids which increase osmotic pressure and oxygen accessibility may also be introduced to the chamber as treatment additives.

Selection of treatment additives is wound specific. For example, if an infection has been diagnosed, antibiotics are added in the amount of one single parenteral dose per 1,000 cc of fluid. Furthermore, a treatment additive of gentamicin, tobramycin or carbenicillin is appropriate for a wound infection with *Pseudomonas*, detected by analyzing extracted fluid. When hypoxia has been diagnosed, the liquid is passed through an oxygenating chamber before entering the chamber. If a tumor has been diagnosed, chemotherapy is given in an amount of one single parenteral dose per 1,000 cc of fluid. In situations involving a wound containing necrotic tissue and debris, proteolytic enzyme is added to the liquid. Immune modulators are added to the treatment fluid if an inflammatory reaction is exhibited. Epidermal growth factor is added in a concentration of 10 nanograms per cc when required.

The present invention will be further understood by reference to the following nonlimiting examples.

EXAMPLES

Example 1

Introduction of DNA into Keratinocytes and Fibroblasts Using "Microseeding"

Iron oxide particles ranging in size from 0.05 microns to 1 micron in diameter were mixed with DNA plasmids in Tris-EDTA buffer. Drops of this material were placed on intact human skin. A microseeding was placed on the material on the skin to insert, or inject, the DNA into superficial keratinocytes as well as stem cell keratinocytes in the deep epidermis, or dermal fibroblasts.

Example 2

Microseeding of Expression Plasmids Into Skin and Wounds, Without Carrier Particles The method of the present invention was tested in a laboratory model system for wound healing. Dorsal skin sites on domestic female Yorkshire pigs (3–4 months old, 40–45 kg) were outlined and were randomly assigned for partial-thickness wound or intact skin treatment. Wounds (15×15×1.2 mm) were created using a dermatome. Animals were maintained in accordance with the Harvard Medical Area Standing Committee on Animals. Surgical procedures were performed under Halothane (1–1.5%) anesthesia in a 3:5 mixture of oxygen and nitrous oxide.

Supercoiled plasmid DNA was introduced into the intact skin or into the wound bed using an oscillating microneedle apparatus driven by an electric motor and a piston. The oscillating microneedle apparatus for external (skin and wound) use is commercially available from Spaulding and Rogers Manufacturing, Inc. (Voorheesville, N.Y.). Controls included skin and wound sites untreated with DNA. 100 μl of solution containing supercoiled plasmid DNA in water was introduced into the intact skin or into the wound bed. After delivery, the skin and wound site were covered with sealed vinyl adhesive chambers, of the type described in U.S. Pat. No. 5,152,757, containing 1.2 ml of isotonic saline with 100 units/ml penicillin and 100 mg/ml streptomycin.

a. Histochemical Determination of Transduced Cells

Plasmid pCMVβ-gal, described by MacGregor, G. R. and C. T. Caskey, *Nucl. Acids Res.*, 17:2365 (1989), was delivered to wound sites. Plasmid pCMVβ-gal encodes a β-galactosidase enzyme which is histochemically detectable upon the addition of 5-bromo-4-chloro-3-indolyl-β-D- galactoside (X-gal chromogen), which forms a blue precipitate in transduced cells. The treated tissues and control tissues were frozen and thin sections prepared from the frozen samples were histochemically stained for β-galactosidase activity. Positive staining was observed only in the epidermal keratinocytes and in the hair follicles of sites treated with pCMVβ-gal DNA. No stained cells were observed in control sections.

Skin biopsies were flash-frozen, embedded in O.C.T. and cut into 8 micron cross-sections. The sections were then fixed in 1.5% glutaraldehyde and were stained for β-galactosidase activity. See MacGregor, G. R. et al., *Somat. Cell Molec. Genet.* 13:253 (1987). The tissues were counterstained with hematoxylin. Blue spots were observed in portions of the tissues having β-galactosidase activity.

b. Delivery of Epidermal Growth Factor-Encoding Plasmid DNA

Plasmid pWRG1630, an epidermal growth factor-encoding expression plasmid, contains an in-frame fusion of the hGH secretory signal peptide to the mature EGF polypeptide. Plasmid pWRG1630 includes, upstream of the chimeric hGH-EGF gene, the cytomegalovirus (CMV) immediate early transcriptional promoter. Downstream of the mature human EGF coding region is the 3' untranslated sequence and polyadenylation signal from the bovine growth hormone gene (obtained from pRc/CMV, commercially available from Invitrogen, Inc.).

The complete nucleotide sequence of plasmid pWRG1630 is attached hereto as SEQ ID NO: 1. The 93 amino acid long polypeptide, encoded in two separate exons by pWRG1630, is shown in SEQ ID NO: 2. Referring now to SEQ ID NO: 2, the hGH secretory signal peptide is the first 26 amino acids. These amino acids are cleaved during signal-peptide processing at a cleavage site between amino acids 26 and 27. The next 14 amino acids are encoded in part by the hGH DNA and in part by the plasmid polylinker. Following the 14 amino acid long portion, is a 53 amino acid long mature EGF portion that corresponds to the 53 amino acids of the naturally occurring mature EGF peptide. The ability of this plasmid to produce an EGF polypeptide has been demonstrated by showing that after transduction of the plasmid into cultured fibroblast KB-3-1 cells, a polypeptide secreted into the culture medium reacted with hEGF monoclonal antibodies in ELISA and Western Blot assays. The culture medium containing the secreted polypeptide was biologically active in an [$^3$H]-thymidine incorporation assay using primary human foreskin fibroblasts and Madine-Darvy Canine Kidney (MDCK) cells.

c. Expression After Delivery

Initial experiments were performed to determine DNA transfer conditions to obtain high specific transfer (expression level per µg of input DNA). Parameters tested included the amount of DNA delivered per wound, the depth of needle penetration, and the density of penetrations. These parameters were adjusted to yield the greatest concentration of hEGF polypeptide in wound fluid after treatment. The preferred conditions for this plasmid were determined to be 20–200 µg of pWRG1630 DNA per wound delivered to a penetration depth of 2 mm at a density of 3,330 penetrations per cm² surface area. In the experiment, 7500 penetrations were performed using the oscillating microneedle apparatus in a 2.25 cm² surface area over a 25 second duration. Microneedles used for microseeding DNA were routinely pre-treated by dipping the tips of the microneedles into hot paraffin and then placing the microneedles into a 35% (12.5M) solution of hydrochloric acid for 12 hours. This pre-treatment scarifies the needles and provides increased surface area for trapping DNA during delivery.

Plasmid pWRG1630 was delivered into wounds at 20 µg, 200 µg or 2,000 µg per wound. At 72 hours post delivery, the wound tissue and the chamber fluid bathing the wound were tested for EGF polypeptide. EGF gene expression was monitored daily after gene transfer by measuring EGF concentrations in wound tissue, intact skin, and wound fluid for at least 7 sites for each group. Wound fluid was withdrawn from the wound chambers every 24 hours. The fluid was immediately chilled on ice, filtered and centrifuged. Samples from each group were then pooled, flash frozen and stored at −70° C. Skin biopsies were homogenized and protein was extracted from the homogenate before analysis. A commercially available EGF ELISA assay (Quantikine, R & D Systems, Minneapolis, Minn.) was used to determine EGF concentrations in samples. The minimum detection limit was 0.2 pg EGF per ml.

When 20 µg of DNA were delivered, between about 25 and 75 (average about 50) pg/ml of EGF were observed.

When 10-fold more EGF-encoding DNA (200 µg) was delivered, both the chamber fluid and the skin extracts contained about 150–175 pg/ml on average. The range of concentrations in the chamber fluid samples was between about 75–250 pg/ml, while the range in the skin extract samples was between about 50–300 pg/ml and was, on average, slightly higher than in the chamber fluid samples.

When yet another 10 fold increase in EGF-encoding DNA (2000 µg) was delivered into wounds, only about a 2 fold increase in EGF concentration was observed over the previous level. In this case, the EGF concentration in the chamber fluid samples ranged from about 250 to about 400 with an average of about 325 pg/ml while the concentration in skin extract samples was, on average, about 400 pg/ml with a range of between about 250 and 575 pg/ml.

From these data, it was determined that a maximally efficient response was observed in the range of 20–200 µg of DNA per wound. In future examples, 20 µg of DNA were delivered per wound or skin site, unless otherwise indicated.

Figure 5:
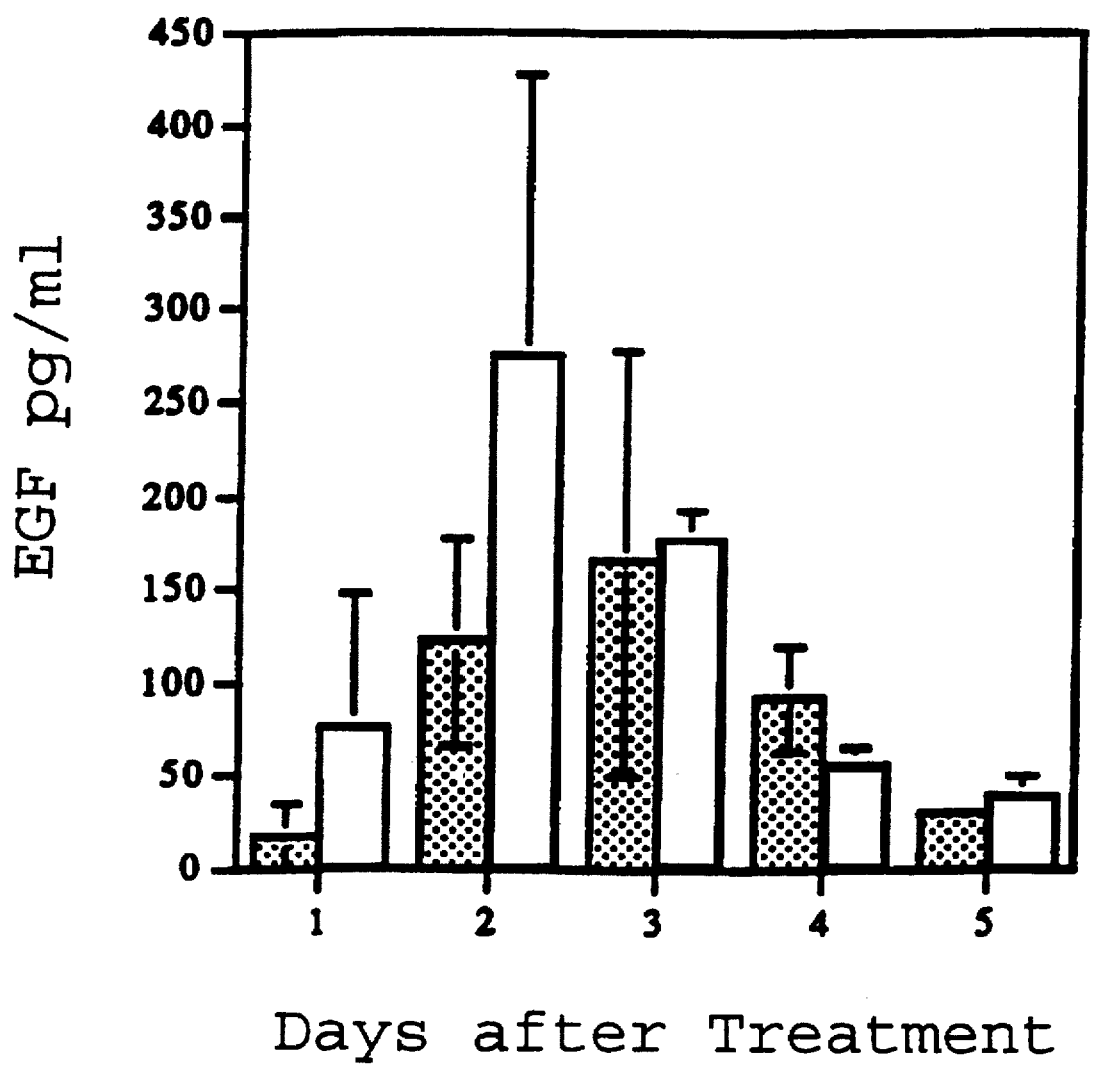
FIG. 5 shows the EGF concentration in target sites at various times after microseeding with an EGF-expressing genetic construct.

Temporal variation in EGF level after gene delivery was monitored in chamber fluid over 5 days. Maximal EGF concentrations in fluid from wound sites (276±149 pg/ml) were observed 48 hours after microseeding. In fluid from intact skin treatment sites, a maximal EGF level of 165±113 pg/ml was observed 72 hours after microseeding. Detectable EGF concentrations were maintained over the entire 5 day monitoring period, as is shown in FIG. 5. The figure shows the EGF concentration in intact skin sites (Stippled) and in wound sites (Filled). Controls from wound sites seeded with 20 µg of pCMVβ-gal, and wound sites treated topically with 20 µg of EGF DNA are not shown. However, no EGF was detected in these controls using the ELISA assay. No evidence of abnormal cell growth, dysplasia tissue disorganization or the like has been observed in cells microseeded with pWRG1630.

d. EGF Yield in Fluid and Tissue after Delivery

Figure 6:
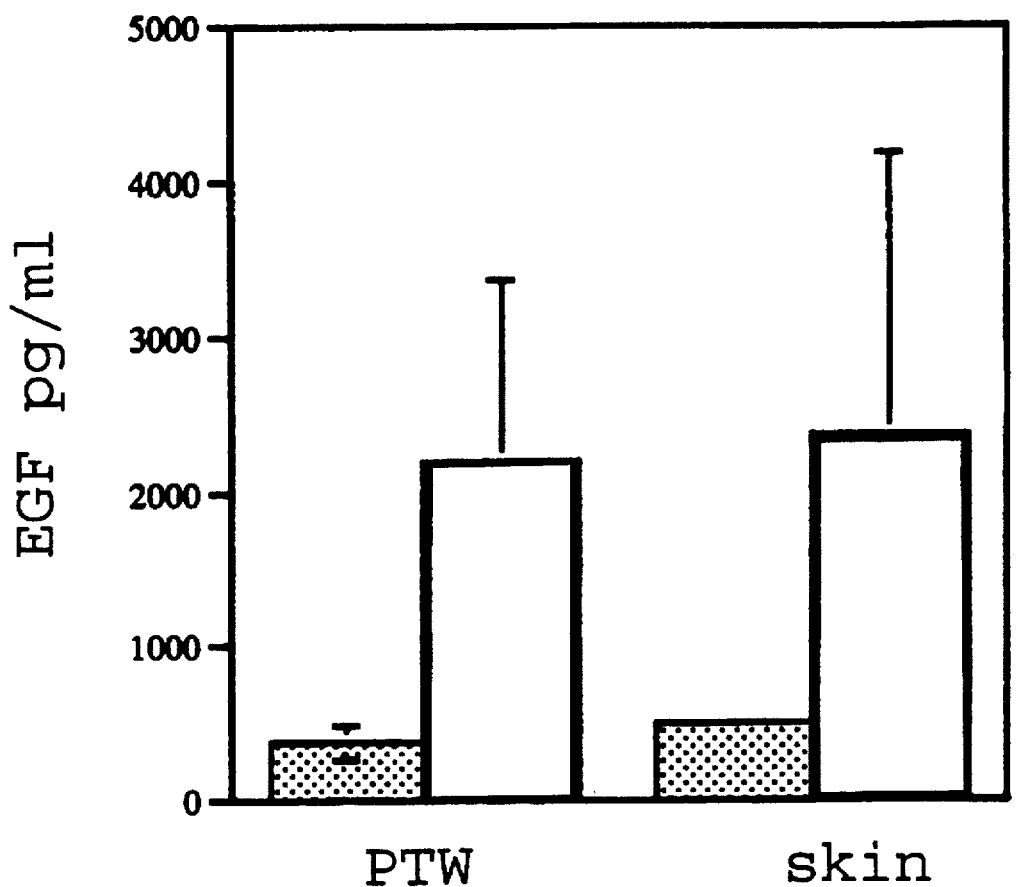
FIG. 6 shows the levels of EGF in fluid and in tissue biopsies taken 3 days after delivery of pWRG1630 into intact skin and into partial thickness wounds.

Three days after delivery of the pWRG1630 EGF-encoding plasmid DNA into partial thickness wounds and into intact skin, analysis of the fluid surrounding the delivery site and of biopsies of the tissue itself were performed to determine the yield of EGF in such tissues. The results shown in FIG. 6 demonstrate that EGF levels in biopsied tissue (filled bars) are much higher than EGF levels in the fluid (stippled bars), and can reach nanogram levels. In FIG. 6, EGF in both wound and intact skin was above 2000 pg (2 ng), on average, and in some samples was above 4000 pg (4 ng), three days after treatment.

e. Persistence of Transferred DNA

Wound biopsy specimens were evaluated using the polymerase chain reaction (PCR) on days 1 through 30 to analyze the persistence of the transgenes. DNA was prepared from wound biopsies on days 6, 9, 12, 15, and 30 after delivery using a Puregene kit, commercially available from Gentra. To monitor for the presence of the introduced DNA, 400 ng of DNA prepared from the wound biopsy was mixed in a PCR reaction with 0.2 μg of each primer and 2.5 units of AmpliTAQ® DNA polymerase (from Perkin Elmer) in 100 μl of 10 mM Tris-HCl, pH 9.0 (25° C.), 50 mM KCl, 0.1% Triton X-100, 1.5 mM MgCl$_2$, and 0.2 mM of each dNTP. The sequences of the primers used are attached hereto as SEQ ID NO: 3 and SEQ ID NO: 4. After 3 minutes at 96° C., the reactions were subjected to 30 cycles of 60° C. for 75 seconds, 72° C. for 60 seconds, 96° C. for 60 seconds. See Mullis, K. B. and F. A. Faloona, Meth. Enzymol. 155:335 (1987). A 10 μl aliquot of each reaction mix was analyzed by agarose gel electrophoresis. The PCR products were visualized by staining with an ethidium bromide and their identities were confirmed by Southern Blot (Southern, E. M., J. Mol. Biol. 98:503 (1975) using internal hybridization probes. The PCR results demonstrated that plasmid DNA persisted in the wound site for at least 30 days. It is as yet unclear whether the persistent DNA resides within cells or is present in the extracellular matrix. These results contrast with the observation that both EGF and β-galactosidase protein expression diminish after 5–6 days.

Example 3

Endoscopic DNA Delivery

An anesthetized Yorkshire pig was placed on its back. Laparoscopic ports were placed into the abdomen to accommodate a viewing scope, an assisting instrument, and a microseeding instrument adapted for use inside the patient as is shown in FIG. 3. A DNA solution containing the pCMVβ-gal plasmid and a small amount of a black iron oxide pigment was delivered to four sites in the liver, two sites in the stomach, and two sites in the abdominal wall. The black iron oxide pigment was added to the DNA solution to facilitate visualization of the treated area after the experiment. The DNA in solution was not coated onto the iron oxide.

Three days later, the tissues were harvested from the pig for processing to visualize expression of the inserted lac-Z gene. Strong expression was observed in the stomach. No expression was found in the liver. Expression in the abdominal wall was questionable. A reference site on the skin that was microseeded as a control showed strong expression. It is possible that the rapid healing of the liver tissue may have obscured the target sites and that the sites were missed during harvesting. In any event, the utility of the microseeding instrument for internal use was demonstrated by the strong lac-Z expression levels in the stomach.

The invention is not intended to be limited to the preferred embodiments nor to the specific examples, but is intended to include all such modifications and variations of the invention as fall within the scope of the appended claims.

We claim:

1. A method for introducing genetic material into a cell the method comprising the step of
repeatedly injecting the genetic material into a plurality of cells of a target tissue at an in situ site on a human or non-human animal with a microneedle, whereby a change in the animal attributable to the delivery of the genetic material is detectable.

2. The method of claim 1 wherein the cell is selected from the group consisting of a superficial keratinocyte, a stem cell keratinocyte, a dermal fibroblast, a smooth muscle, a striated muscle, a connective tissue, an epithelial tissue, a wall of an abdominal passage, a liver, a kidney, a stomach, an appendix, an intestine, a pancreas, a lung, a heart, a bladder, a gall bladder, a brain, an endocrine gland, a reproductive gland, and a lymphatic gland.

3. The method of claim 1 wherein the genetic material is attached to microparticles.

4. The method of claim 3 wherein the microparticles are iron oxide particles ranging in size from 0.5 to 1 micron in diameter.

5. A method for delivering genetic material into a human or non-human subject, the method comprising the steps of:
contacting a tip of a microneedle with a solution comprising the genetic material;
penetrating the tip repeatedly into a site on a surface of a target tissue at an in situ site on the subject, to a depth in the tissue selected to allow contact between the tip and a plurality of target cells that can take up the genetic material, until a sufficient amount of the genetic material is delivered to the target cells such that a change in the subject attributable to the delivery of the genetic material is detectable.

6. A method as claimed in claim 5 wherein the target tissue is selected from the group consisting of skin cells and a wound.

7. A method as claimed in claim 5 wherein the target tissue is internal to the subject.

8. A method as claimed in claim 7 wherein the target tissue is selected from the group consisting of a smooth muscle, a striated muscle, a connective tissue, an epithelial tissue, a wall of an abdominal passage, a liver, a kidney, a stomach, an appendix, an intestine, a pancreas, a lung, a heart, a bladder, a gall bladder, a brain, an endocrine gland, a reproductive gland, and a lymphatic gland.

9. A method as claimed in claim 5 wherein less than about 500 micrograms of the genetic construct are delivered to the target cells.

10. A method as claimed in claim 5 wherein between about 20 and 200 micrograms of the genetic construct are delivered to the target cells.

11. A method as claimed in claim 5 wherein the penetrating step is repeated between about 500 and 5000 times per cm² of the surface of the target tissue.

12. A method as claimed in claim 5 wherein the penetrating step is repeated between 3000 and 4000 times per cm² of the surface of the target tissue.

13. A method as claimed in claim 5 wherein the tip penetrates the target tissue to a depth of less than 5 mm.

14. A method as claimed in claim 5 wherein the tip penetrates the target tissue to a depth of less than 3 mm.

15. A method as claimed in claim 5 wherein the genetic material encodes a non-native growth factor.

16. A method as claimed in claim 15 wherein the non-native growth factor is epidermal growth factor.

17. A method as claimed in claim 5 wherein the subject is non-human.

18. A method as claimed in claim 17 wherein the subject is selected from a group consisting of a dog, a cat, cattle, swine, a goat, and a sheep.

19. A method as claimed in claim 5 wherein the subject is a human.

20. A method as claimed in claim 5 further comprising the step of:
   placing the microneedle in a concentrated solution of hydrochloric acid before the penetrating step.

21. A method for delivering genetic material into a target tissue of a subject, the method comprising the steps of:
   contacting a tip of a microneedle with a solution comprising the genetic material;
   penetrating the tip repeatedly into a site on a surface of the target tissue, to a depth selected to allow contact between the tip and a plurality of target cells that can take up the genetic material, until a sufficient amount of the genetic material is delivered to the target cells such that a change in the subject attributable to the delivery of the genetic material is detectable,
   wherein the target tissue is selected from the group consisting of skin cells and a wound, the method further comprising the step of covering the target cells with a protective chamber.

* * * * *